US012805949B2

(12) United States Patent
Hagn

(10) Patent No.: US 12,805,949 B2
(45) Date of Patent: Nov. 24, 2026

(54) LINEAR TRANSMISSION MECHANISM FOR ACTUATING A PRISMATIC JOINT OF A SURGICAL ROBOT

(71) Applicant: Covidien LP, Mansfield, MA (US)

(72) Inventor: Ulrich Hagn, Munich (DE)

(73) Assignee: Covidien LP, Mansfield, MA (US)

( * ) Notice: Subject to any disclaimer, the term of this patent is extended or adjusted under 35 U.S.C. 154(b) by 212 days.

(21) Appl. No.: 18/697,819

(22) PCT Filed: Nov. 7, 2022

(86) PCT No.: PCT/IB2022/060688
§ 371 (c)(1),
(2) Date: Apr. 2, 2024

(87) PCT Pub. No.: WO2023/079521
PCT Pub. Date: May 11, 2023

(65) Prior Publication Data

US 2024/0407864 A1 Dec. 12, 2024

Related U.S. Application Data

(60) Provisional application No. 63/276,726, filed on Nov. 8, 2021.

(51) Int. Cl.
*A61B 34/30* (2016.01)

(52) U.S. Cl.
CPC .................................... *A61B 34/30* (2016.02)

(58) Field of Classification Search
None
See application file for complete search history.

(56) References Cited

U.S. PATENT DOCUMENTS

| | | | | |
|---|---|---|---|---|
| 6,132,368 | A | 10/2000 | Cooper | |
| 6,206,903 | B1 | 3/2001 | Ramans | |
| 6,246,200 | B1 | 6/2001 | Blumenkranz et al. | |
| 6,312,435 | B1 | 11/2001 | Wallace et al. | |
| 6,324,934 | B1 * | 12/2001 | Monaghan | B25J 19/0029 901/21 |
| 6,331,181 | B1 | 12/2001 | Tierney et al. | |
| 6,394,998 | B1 | 5/2002 | Wallace et al. | |
| 6,424,885 | B1 | 7/2002 | Niemeyer et al. | |
| 6,441,577 | B2 | 8/2002 | Blumenkranz et al. | |
| 6,459,926 | B1 | 10/2002 | Nowlin et al. | |
| 6,491,691 | B1 | 12/2002 | Morley et al. | |
| 6,491,701 | B2 | 12/2002 | Tierney et al. | |

(Continued)

FOREIGN PATENT DOCUMENTS

| | | |
|---|---|---|
| CN | 109091238 A | 12/2018 |
| CN | 107157581 B | 2/2020 |
| CN | 210019644 U | 2/2020 |

OTHER PUBLICATIONS

International Search Report and Written Opinion of the International Searching Authority issued in corresponding application PCT/IB2022/060688 mailed Feb. 2, 2023 (11 pages).

*Primary Examiner* — Shirley X Jian
(74) *Attorney, Agent, or Firm* — Carter, DeLuca & Farrell LLP

(57) ABSTRACT

A robotic arm with a linear transmission mechanism for a surgical robotic system. The robotic arm includes a first link pivotally coupled to a second link at a first joint and a holder pivotally coupled to the second link at a second joint.

16 Claims, 5 Drawing Sheets

(56) References Cited

U.S. PATENT DOCUMENTS 6,493,608 B1 12/2002 Niemeyer
6,565,554 B1 5/2003 Niemeyer
6,645,196 B1 11/2003 Nixon et al.
6,659,939 B2 12/2003 Moll
6,671,581 B2 12/2003 Niemeyer et al.
6,676,684 B1 1/2004 Morley et al.
6,685,698 B2 2/2004 Morley et al.
6,699,235 B2 3/2004 Wallace et al.
6,714,839 B2 3/2004 Salisbury, Jr. et al.
6,716,233 B1 4/2004 Whitman
6,728,599 B2 4/2004 Wang et al.
6,746,443 B1 6/2004 Morley et al.
6,766,204 B2 7/2004 Niemeyer et al.
6,770,081 B1 8/2004 Cooper et al.
6,772,053 B2 8/2004 Niemeyer
6,783,524 B2 8/2004 Anderson et al.
6,793,652 B1 9/2004 Whitman et al.
6,793,653 B2 9/2004 Sanchez et al.
6,799,065 B1 9/2004 Niemeyer
6,837,883 B2 1/2005 Moll et al.
6,839,612 B2 1/2005 Sanchez et al.
6,840,938 B1 1/2005 Morley et al.
6,843,403 B2 1/2005 Whitman
6,846,309 B2 1/2005 Whitman et al.
6,866,671 B2 3/2005 Tierney et al.
6,871,117 B2 3/2005 Wang et al.
6,879,880 B2 4/2005 Nowlin et al.
6,899,705 B2 5/2005 Niemeyer
6,902,560 B1 6/2005 Morley et al.
6,936,042 B2 8/2005 Wallace et al.
6,951,535 B2 10/2005 Ghodoussi et al.
6,974,449 B2 12/2005 Niemeyer
6,991,627 B2 1/2006 Madhani et al.
6,994,708 B2 2/2006 Manzo
7,048,745 B2 5/2006 Tierney et al.
7,066,926 B2 6/2006 Wallace et al.
7,118,582 B1 10/2006 Wang et al.
7,125,403 B2 10/2006 Julian et al.
7,155,315 B2 12/2006 Niemeyer et al.
7,239,940 B2 7/2007 Wang et al.
7,306,597 B2 12/2007 Manzo
7,357,774 B2 4/2008 Cooper
7,373,219 B2 5/2008 Nowlin et al.
7,379,790 B2 5/2008 Toth et al.
7,386,365 B2 6/2008 Nixon
7,391,173 B2 6/2008 Schena
7,398,707 B2 7/2008 Morley et al.
7,413,565 B2 8/2008 Wang et al.
7,453,227 B2 11/2008 Prisco et al.
7,524,320 B2 4/2009 Tierney et al.
7,574,250 B2 8/2009 Niemeyer
7,594,912 B2 9/2009 Cooper et al.
7,607,440 B2 10/2009 Coste-Maniere et al.
7,666,191 B2 2/2010 Orban, III et al.
7,682,357 B2 3/2010 Ghodoussi et al.
7,689,320 B2 3/2010 Prisco et al.
7,695,481 B2 4/2010 Wang et al.
7,695,485 B2 4/2010 Whitman et al.
7,699,855 B2 4/2010 Anderson et al.
7,713,263 B2 5/2010 Niemeyer
7,725,214 B2 5/2010 Diolaiti
7,727,244 B2 6/2010 Orban, III et al.
7,741,802 B2 6/2010 Prisco
7,756,036 B2 7/2010 Druke et al.
7,757,028 B2 7/2010 Druke et al.
7,762,825 B2 7/2010 Burbank et al.
7,778,733 B2 8/2010 Nowlin et al.
7,803,151 B2 9/2010 Whitman
7,806,891 B2 10/2010 Nowlin et al.
7,819,859 B2 10/2010 Prisco et al.
7,819,885 B2 10/2010 Cooper
7,824,401 B2 11/2010 Manzo et al.
7,835,823 B2 11/2010 Sillman et al.
7,843,158 B2 11/2010 Prisco
7,865,266 B2 1/2011 Moll et al.
7,865,269 B2 1/2011 Prisco et al.
7,886,743 B2 2/2011 Cooper et al.
7,899,578 B2 3/2011 Prisco et al.
7,907,166 B2 3/2011 Lamprecht et al.
7,935,130 B2 5/2011 Williams
7,963,913 B2 6/2011 Devengenzo et al.
7,983,793 B2 7/2011 Toth et al.
8,002,767 B2 8/2011 Sanchez
8,004,229 B2 8/2011 Nowlin et al.
8,012,170 B2 9/2011 Whitman et al.
8,054,752 B2 11/2011 Druke et al.
8,062,288 B2 11/2011 Cooper et al.
8,079,950 B2 12/2011 Stern et al.
8,100,133 B2 1/2012 Mintz et al.
8,108,072 B2 1/2012 Zhao et al.
8,120,301 B2 2/2012 Goldberg et al.
8,142,447 B2 3/2012 Cooper et al.
8,147,503 B2 4/2012 Zhao et al.
8,151,661 B2 4/2012 Schena et al.
8,155,479 B2 4/2012 Hoffman et al.
8,182,469 B2 5/2012 Anderson et al.
8,202,278 B2 6/2012 Orban, III et al.
8,206,406 B2 6/2012 Orban, III
8,210,413 B2 7/2012 Whitman et al.
8,216,250 B2 7/2012 Orban, III et al.
8,220,468 B2 7/2012 Cooper et al.
8,256,319 B2 9/2012 Cooper et al.
8,285,517 B2 10/2012 Sillman et al.
8,315,720 B2 11/2012 Mohr et al.
8,335,590 B2 12/2012 Costa et al.
8,347,757 B2 1/2013 Duval
8,374,723 B2 2/2013 Zhao et al.
8,418,073 B2 4/2013 Mohr et al.
8,419,717 B2 4/2013 Diolaiti et al.
8,423,182 B2 4/2013 Robinson et al.
8,452,447 B2 5/2013 Nixon
8,454,585 B2 6/2013 Whitman
8,499,992 B2 8/2013 Whitman et al.
8,508,173 B2 8/2013 Goldberg et al.
8,528,440 B2 9/2013 Morley et al.
8,529,582 B2 9/2013 Devengenzo et al.
8,540,748 B2 9/2013 Murphy et al.
8,551,116 B2 10/2013 Julian et al.
8,562,594 B2 10/2013 Cooper et al.
8,594,841 B2 11/2013 Zhao et al.
8,597,182 B2 12/2013 Stein et al.
8,597,280 B2 12/2013 Cooper et al.
8,600,551 B2 12/2013 Itkowitz et al.
8,608,773 B2 12/2013 Tierney et al.
8,620,473 B2 12/2013 Diolaiti et al.
8,624,537 B2 1/2014 Nowlin et al.
8,634,957 B2 1/2014 Toth et al.
8,638,056 B2 1/2014 Goldberg et al.
8,638,057 B2 1/2014 Goldberg et al.
8,644,988 B2 2/2014 Prisco et al.
8,666,544 B2 3/2014 Moll et al.
8,668,638 B2 3/2014 Donhowe et al.
8,746,252 B2 6/2014 McGrogan et al.
8,749,189 B2 6/2014 Nowlin et al.
8,749,190 B2 6/2014 Nowlin et al.
8,758,352 B2 6/2014 Cooper et al.
8,761,930 B2 6/2014 Nixon
8,768,516 B2 7/2014 Diolaiti et al.
8,786,241 B2 7/2014 Nowlin et al.
8,790,243 B2 7/2014 Cooper et al.
8,808,164 B2 8/2014 Hoffman et al.
8,816,628 B2 8/2014 Nowlin et al.
8,821,480 B2 9/2014 Burbank
8,823,308 B2 9/2014 Nowlin et al.
8,827,989 B2 9/2014 Niemeyer
8,838,270 B2 9/2014 Druke et al.
8,852,174 B2 10/2014 Burbank
8,858,547 B2 10/2014 Brogna
8,862,268 B2 10/2014 Robinson et al.
8,864,751 B2 10/2014 Prisco et al.
8,864,752 B2 10/2014 Diolaiti et al.
8,903,546 B2 12/2014 Diolaiti et al.
8,903,549 B2 12/2014 Itkowitz et al.
8,911,428 B2 12/2014 Cooper et al.

(56) References Cited

U.S. PATENT DOCUMENTS 8,912,746 B2 12/2014 Reid et al.
8,944,070 B2 2/2015 Guthart
8,989,903 B2 3/2015 Weir et al.
9,002,518 B2 4/2015 Manzo
9,014,856 B2 4/2015 Manzo et al.
9,016,540 B2 4/2015 Whitman et al.
9,019,345 B2 4/2015 O'Grady et al.
9,027,431 B2 5/2015 Tang et al.
9,043,027 B2 5/2015 Durant et al.
9,050,120 B2 6/2015 Swarup et al.
9,055,961 B2 6/2015 Manzo et al.
9,068,628 B2 * 6/2015 Solomon ................ A61B 34/30
9,078,684 B2 7/2015 Williams
9,084,623 B2 7/2015 Gomez et al.
9,095,362 B2 8/2015 Dachs, II et al.
9,096,033 B2 8/2015 Holop et al.
9,101,381 B2 8/2015 Burbank et al.
9,113,877 B1 8/2015 Whitman et al.
9,138,284 B2 9/2015 Krom et al.
9,144,456 B2 9/2015 Rosa et al.
9,198,730 B2 12/2015 Prisco et al.
9,204,923 B2 12/2015 Manzo et al.
9,226,648 B2 1/2016 Saadat et al.
9,226,750 B2 1/2016 Weir et al.
9,226,761 B2 1/2016 Burbank
9,232,984 B2 1/2016 Guthart et al.
9,241,766 B2 1/2016 Duque et al.
9,241,767 B2 1/2016 Prisco et al.
9,241,769 B2 1/2016 Larkin et al.
9,259,275 B2 2/2016 Burbank
9,259,277 B2 2/2016 Rogers et al.
9,259,281 B2 2/2016 Griffiths et al.
9,259,282 B2 2/2016 Azizian et al.
9,261,172 B2 * 2/2016 Solomon .................. B25J 18/00
9,265,567 B2 2/2016 Orban, III et al.
9,265,584 B2 2/2016 Itkowitz et al.
9,283,043 B2 3/2016 Tsao et al.
9,283,049 B2 3/2016 Diolaiti et al.
9,301,811 B2 4/2016 Goldberg et al.
9,314,307 B2 4/2016 Richmond et al.
9,317,651 B2 4/2016 Nixon
9,345,546 B2 5/2016 Toth et al.
9,393,017 B2 7/2016 Flanagan et al.
9,402,689 B2 8/2016 Prisco et al.
9,417,621 B2 8/2016 Diolaiti
9,424,303 B2 8/2016 Hoffman et al.
9,433,418 B2 9/2016 Whitman et al.
9,446,517 B2 9/2016 Burns et al.
9,452,020 B2 9/2016 Griffiths et al.
9,474,569 B2 10/2016 Manzo et al.
9,480,533 B2 11/2016 Devengenzo et al.
9,503,713 B2 11/2016 Zhao et al.
9,550,300 B2 1/2017 Danitz et al.
9,554,859 B2 1/2017 Nowlin et al.
9,566,124 B2 2/2017 Prisco et al.
9,579,164 B2 2/2017 Itkowitz et al.
9,585,641 B2 3/2017 Cooper et al.
9,615,883 B2 4/2017 Schena et al.
9,623,563 B2 4/2017 Nixon
9,623,902 B2 4/2017 Griffiths et al.
9,629,520 B2 4/2017 Diolaiti
9,655,680 B2 5/2017 Shim et al.
9,662,177 B2 5/2017 Weir et al.
9,664,262 B2 5/2017 Donlon et al.
9,675,354 B2 6/2017 Weir et al.
9,687,312 B2 6/2017 Dachs, II et al.
9,700,334 B2 7/2017 Hinman et al.
9,718,190 B2 8/2017 Larkin et al.
9,730,719 B2 8/2017 Brisson et al.
9,737,199 B2 8/2017 Pistor et al.
9,795,446 B2 10/2017 DiMaio et al.
9,797,484 B2 10/2017 Solomon et al.
9,801,690 B2 10/2017 Larkin et al.
9,803,727 B2 * 10/2017 Solomon ................ B25J 18/007
9,814,530 B2 11/2017 Weir et al.
9,814,536 B2 11/2017 Goldberg et al.
9,814,537 B2 11/2017 Itkowitz et al.
9,820,823 B2 11/2017 Richmond et al.
9,827,059 B2 11/2017 Robinson et al.
9,830,371 B2 11/2017 Hoffman et al.
9,839,481 B2 12/2017 Blumenkranz et al.
9,839,487 B2 12/2017 Dachs, II
9,850,994 B2 12/2017 Schena
9,855,102 B2 1/2018 Blumenkranz
9,855,107 B2 1/2018 Labonville et al.
9,872,737 B2 1/2018 Nixon
9,877,718 B2 1/2018 Weir et al.
9,883,920 B2 2/2018 Blumenkranz
9,888,974 B2 2/2018 Niemeyer
9,895,813 B2 2/2018 Blumenkranz et al.
9,901,408 B2 2/2018 Larkin
9,918,800 B2 3/2018 Itkowitz et al.
9,943,375 B2 4/2018 Blumenkranz et al.
9,948,852 B2 4/2018 Lilagan et al.
9,949,798 B2 4/2018 Weir
9,949,802 B2 4/2018 Cooper
9,952,107 B2 4/2018 Blumenkranz et al.
9,956,044 B2 5/2018 Gomez et al.
9,980,778 B2 5/2018 Ohline et al.
10,008,017 B2 6/2018 Itkowitz et al.
10,028,793 B2 7/2018 Griffiths et al.
10,033,308 B2 7/2018 Chaghajerdi et al.
10,034,719 B2 7/2018 Richmond et al.
10,052,167 B2 8/2018 Au et al.
10,085,811 B2 10/2018 Weir et al.
10,092,165 B2 10/2018 Power
10,092,344 B2 10/2018 Mohr et al.
10,123,844 B2 11/2018 Nowlin
10,188,471 B2 1/2019 Brisson
10,201,390 B2 2/2019 Swarup et al.
10,213,202 B2 2/2019 Flanagan et al.
10,258,416 B2 4/2019 Mintz et al.
10,278,782 B2 5/2019 Jarc et al.
10,278,783 B2 5/2019 Itkowitz et al.
10,282,881 B2 5/2019 Itkowitz et al.
10,335,242 B2 7/2019 Devengenzo et al.
10,405,934 B2 9/2019 Prisco et al.
10,433,922 B2 10/2019 Itkowitz et al.
10,464,219 B2 11/2019 Robinson et al.
10,485,621 B2 11/2019 Morrissette et al.
10,500,004 B2 12/2019 Hanuschik et al.
10,500,005 B2 12/2019 Weir et al.
10,500,007 B2 12/2019 Richmond et al.
10,507,066 B2 12/2019 DiMaio et al.
10,510,267 B2 12/2019 Jarc et al.
10,524,871 B2 1/2020 Liao
10,548,459 B2 2/2020 Itkowitz et al.
10,575,909 B2 3/2020 Robinson et al.
10,592,529 B2 3/2020 Hoffman et al.
10,595,946 B2 3/2020 Nixon
10,646,292 B2 * 5/2020 Solomon ................ A61B 34/37
10,828,115 B2 11/2020 Koenig et al.
10,881,469 B2 1/2021 Robinson
10,881,473 B2 1/2021 Itkowitz et al.
10,898,188 B2 1/2021 Burbank
10,898,189 B2 1/2021 McDonald, II
10,905,506 B2 2/2021 Itkowitz et al.
10,912,544 B2 2/2021 Brisson et al.
10,912,619 B2 2/2021 Jarc et al.
10,918,387 B2 2/2021 Duque et al.
10,918,449 B2 2/2021 Solomon et al.
10,932,873 B2 3/2021 Griffiths et al.
10,932,877 B2 3/2021 Devengenzo et al.
10,939,969 B2 3/2021 Swarup et al.
10,939,973 B2 3/2021 DiMaio et al.
10,952,801 B2 3/2021 Miller et al.
10,965,933 B2 3/2021 Jarc
10,966,742 B2 4/2021 Rosa et al.
10,973,517 B2 4/2021 Wixey
10,973,519 B2 4/2021 Weir et al.
10,984,567 B2 4/2021 Itkowitz et al.
10,993,773 B2 5/2021 Cooper et al.
10,993,775 B2 5/2021 Cooper et al.
11,000,331 B2 5/2021 Krom et al.

(56) References Cited

U.S. PATENT DOCUMENTS

| | | | |
|---|---|---|---|
| 11,013,567 B2 | 5/2021 | Wu et al. | |
| 11,020,138 B2 | 6/2021 | Ragosta | |
| 11,020,191 B2 | 6/2021 | Diolaiti et al. | |
| 11,020,193 B2 | 6/2021 | Wixey et al. | |
| 11,026,755 B2 | 6/2021 | Weir et al. | |
| 11,026,759 B2 | 6/2021 | Donlon et al. | |
| 11,040,189 B2 | 6/2021 | Vaders et al. | |
| 11,045,077 B2 | 6/2021 | Stern et al. | |
| 11,045,274 B2 | 6/2021 | Dachs, II et al. | |
| 11,058,501 B2 | 7/2021 | Tokarchuk et al. | |
| 11,076,925 B2 | 8/2021 | DiMaio et al. | |
| 11,090,119 B2 | 8/2021 | Burbank | |
| 11,096,687 B2 | 8/2021 | Flanagan et al. | |
| 11,098,803 B2 | 8/2021 | Duque et al. | |
| 11,109,925 B2 | 9/2021 | Cooper et al. | |
| 11,116,578 B2 | 9/2021 | Hoffman et al. | |
| 11,129,683 B2 | 9/2021 | Steger et al. | |
| 11,135,029 B2 | 10/2021 | Suresh et al. | |
| 11,147,552 B2 | 10/2021 | Burbank et al. | |
| 11,147,640 B2 | 10/2021 | Jarc et al. | |
| 11,154,373 B2 | 10/2021 | Abbott et al. | |
| 11,154,374 B2 | 10/2021 | Hanuschik et al. | |
| 11,160,622 B2 | 11/2021 | Goldberg et al. | |
| 11,160,625 B2 | 11/2021 | Wixey et al. | |
| 11,161,243 B2 | 11/2021 | Rabindran et al. | |
| 11,166,758 B2 | 11/2021 | Mohr et al. | |
| 11,166,770 B2 | 11/2021 | DiMaio et al. | |
| 11,166,773 B2 | 11/2021 | Ragosta et al. | |
| 11,173,597 B2 | 11/2021 | Rabindran et al. | |
| 11,185,378 B2 | 11/2021 | Weir et al. | |
| 11,191,596 B2 | 12/2021 | Thompson et al. | |
| 11,197,729 B2 | 12/2021 | Thompson et al. | |
| 11,213,360 B2 | 1/2022 | Hourtash et al. | |
| 11,221,863 B2 | 1/2022 | Azizian et al. | |
| 11,234,700 B2 | 2/2022 | Ragosta et al. | |
| 11,241,274 B2 | 2/2022 | Vaders et al. | |
| 11,241,290 B2 | 2/2022 | Waterbury et al. | |
| 11,259,870 B2 | 3/2022 | DiMaio et al. | |
| 11,259,884 B2 | 3/2022 | Burbank | |
| 11,272,993 B2 | 3/2022 | Gomez et al. | |
| 11,272,994 B2 | 3/2022 | Saraliev et al. | |
| 11,291,442 B2 | 4/2022 | Wixey et al. | |
| 11,291,513 B2 | 4/2022 | Manzo et al. | |
| 11,376,002 B2 | 7/2022 | Shelton, IV et al. | |
| 11,376,098 B2 | 7/2022 | Shelton, IV et al. | |
| 11,381,759 B2 | 7/2022 | Zhao et al. | |
| 11,382,621 B2 | 7/2022 | Scheib et al. | |
| 11,382,624 B2 | 7/2022 | Harris et al. | |
| 11,382,625 B2 | 7/2022 | Huitema et al. | |
| 11,382,626 B2 | 7/2022 | Shelton, IV et al. | |
| 11,382,627 B2 | 7/2022 | Huitema et al. | |
| 11,382,638 B2 | 7/2022 | Harris et al. | |
| 11,382,644 B2 | 7/2022 | Schoettgen et al. | |
| 11,389,160 B2 | 7/2022 | Shelton, IV et al. | |
| 11,389,255 B2 | 7/2022 | DiMaio et al. | |
| 11,399,906 B2 | 8/2022 | Shelton, IV et al. | |
| 11,406,379 B2 | 8/2022 | Hess et al. | |
| 11,410,259 B2 | 8/2022 | Harris et al. | |
| 11,419,630 B2 | 8/2022 | Yates et al. | |
| 11,424,027 B2 | 8/2022 | Shelton, IV | |
| 11,432,888 B2 | 9/2022 | Diolaiti et al. | |
| 11,432,893 B2 | 9/2022 | Itkowitz et al. | |
| 11,432,895 B2 | 9/2022 | Loh et al. | |
| 11,439,390 B2 | 9/2022 | Patel et al. | |
| 11,439,391 B2 | 9/2022 | Bruns et al. | |
| 11,468,791 B2 | 10/2022 | Jarc et al. | |
| 11,471,155 B2 | 10/2022 | Shelton, IV et al. | |
| 11,471,221 B2 | 10/2022 | Zhao et al. | |
| 11,478,308 B2 | 10/2022 | Hoffman et al. | |
| 11,490,977 B2 | 11/2022 | Schena et al. | |
| 11,497,499 B2 | 11/2022 | Shelton, IV et al. | |
| 11,504,119 B2 | 11/2022 | Shelton, IV et al. | |
| 11,504,124 B2 | 11/2022 | Patel et al. | |
| 11,510,743 B2 | 11/2022 | Shelton, IV et al. | |
| 11,517,312 B2 | 12/2022 | Wixey | |
| 11,517,325 B2 | 12/2022 | Shelton, IV et al. | |
| 11,518,048 B2 | 12/2022 | Saraliev et al. | |
| 11,957,427 B2 * | 4/2024 | Fenech | A61B 34/35 |
| 2007/0089557 A1 * | 4/2007 | Solomon | A61B 34/71<br>74/490.01 |
| 2009/0087288 A1 * | 4/2009 | Hofmeister | B25J 18/00<br>414/222.01 |
| 2013/0239735 A1 * | 9/2013 | Solomon | A61B 34/71<br>901/21 |
| 2013/0244820 A1 * | 9/2013 | Solomon | B25J 18/00<br>474/58 |
| 2018/0079074 A1 * | 3/2018 | Devengenzo | A61B 1/00149 |
| 2020/0205645 A1 * | 7/2020 | Hashimoto | B25J 9/0009 |
| 2021/0030501 A1 | 2/2021 | Eyre et al. | |
| 2021/0378771 A1 * | 12/2021 | Fenech | A61B 34/35 |

* cited by examiner

LINEAR TRANSMISSION MECHANISM FOR ACTUATING A PRISMATIC JOINT OF A SURGICAL ROBOT

CROSS REFERENCE TO RELATED APPLICATIONS

The present application is a U.S. National Stage Application filed under 35 U.S.C. § 371(a) of International Patent Application No. PCT/IB2022/060688, filed on Nov. 7, 2022, which claims the benefit of and priority to U.S. Provisional Application No. 63/276,726, filed on Nov. 8, 2021. The entire disclosures of the foregoing applications are incorporated by reference herein.

FIELD

The present disclosure generally relates to a surgical robotic system having a robotic arm with a linear transmission mechanism.

BACKGROUND

Surgical robotic systems are currently being used in minimally invasive medical procedures. Some surgical robotic systems include a surgical console controlling a surgical robotic arm and a surgical instrument having an end effector (e.g., forceps or grasping instrument) coupled to and actuated by the robotic arm.

The surgical robotic arm may have multiple links and joints enabling versatile movements of the portions of the robotic arm and components coupled thereto.

SUMMARY

According to one aspect of the present disclosure, a robotic arm for a surgical robotic system is disclosed and includes a first link, a second link, a holder, and an instrument drive unit. The first link is pivotally coupled to the second link at a first joint and the holder is pivotally coupled to the second link at a second joint. The first link includes an actuator and the second link includes a first belt operably coupled to the actuator. The holder includes a first pulley, a second pulley, and a second belt coupled to the first pulley and the second pulley. The instrument drive unit is operably coupled to the second belt and configured to move linearly along a longitudinal axis of the holder.

In an aspect, rotation of the actuator in a first direction causes the instrument drive unit to move along the longitudinal axis of the holder in a first linear direction and wherein rotation of the actuator in a second direction causes the instrument drive unit to move along the longitudinal axis of the holder in a second linear direction opposite the first linear direction.

In an aspect, the instrument drive unit is removably coupled to the second belt.

In an aspect, a surgical instrument is operably coupled to the instrument drive unit.

In an aspect, the actuator is integrated into the first link and is configured to produce an output oriented coaxially with the first joint.

In an aspect, the first pulley is coupled to the first belt at the second joint.

In an aspect, a third link is coupled to the first link at a third joint.

In an aspect, a second actuator is disposed at the third joint. Additionally or alternatively, the first link further includes a third belt operably coupled to the second actuator. In an aspect, actuation of the second actuator causes the first link to pivot relative to the third link and the second link.

In an aspect, angle between the holder and the first link does not change upon movement of the second link relative to the first link.

According to another aspect of the present disclosure, a robotic surgical system is disclosed and includes a movable cart and a robotic arm operably coupled to the movable cart. The robotic arm includes a first link, a second link, a holder, and an instrument drive unit. The first link is pivotally coupled to the second link at a first joint and the holder is pivotally coupled to the second link at a second joint. The first link includes an actuator and the second link includes a first belt operably coupled to the actuator. The holder includes a first pulley, a second pulley, and a second belt coupled to the first pulley and the second pulley. The instrument drive unit is operably coupled to the second belt and configured to move linearly along a longitudinal axis of the holder.

In an aspect, rotation of the actuator in a first direction causes the instrument drive unit to move along the longitudinal axis of the holder in a first linear direction and wherein rotation of the actuator in a second direction causes the instrument drive unit to move along the longitudinal axis of the holder in a second linear direction opposite the first linear direction.

In an aspect, the instrument drive unit is removably coupled to the second belt.

In an aspect, a surgical instrument is operably coupled to the instrument drive unit.

In an aspect, the actuator is integrated into the first link and is configured to produce an output oriented coaxially with the first joint.

In an aspect, the first pulley is coupled to the first belt at the second joint.

In an aspect, a third link is coupled to the first link at a third joint.

In an aspect, a second actuator is disposed at the third joint. Additionally or alternatively, the first link further includes a third belt operably coupled to the second actuator. In an aspect, actuation of the second actuator causes the first link to pivot relative to the third link and the second link.

In an aspect, angle between the holder and the first link does not change upon movement of the second link relative to the first link.

BRIEF DESCRIPTION OF THE DRAWINGS

Various embodiments of the present disclosure are described herein with reference to the drawings, wherein.

DETAILED DESCRIPTION

The term "application" may include a computer program designed to perform functions, tasks, or activities for the benefit of a user. Application may refer to, for example, software running locally or remotely, as a standalone program or in a web browser, or other software which would be understood by one skilled in the art to be an application. An application may run on a controller, or on a user device, including, for example, a mobile device, an IoT device, or a server system.

As will be described in detail below, the present disclosure is directed to a surgical robotic system, which includes a surgical console, a control tower, and one or more movable carts having a surgical robotic arm coupled to a setup arm. The surgical console receives user input through one or more interface devices, which are interpreted by the control tower as movement commands for moving the surgical robotic arm. The surgical robotic arm includes a controller, which is configured to process the movement command and to generate a torque command for activating one or more actuators of the robotic arm, which would, in turn, move the robotic arm in response to the movement command.

Figure 1:
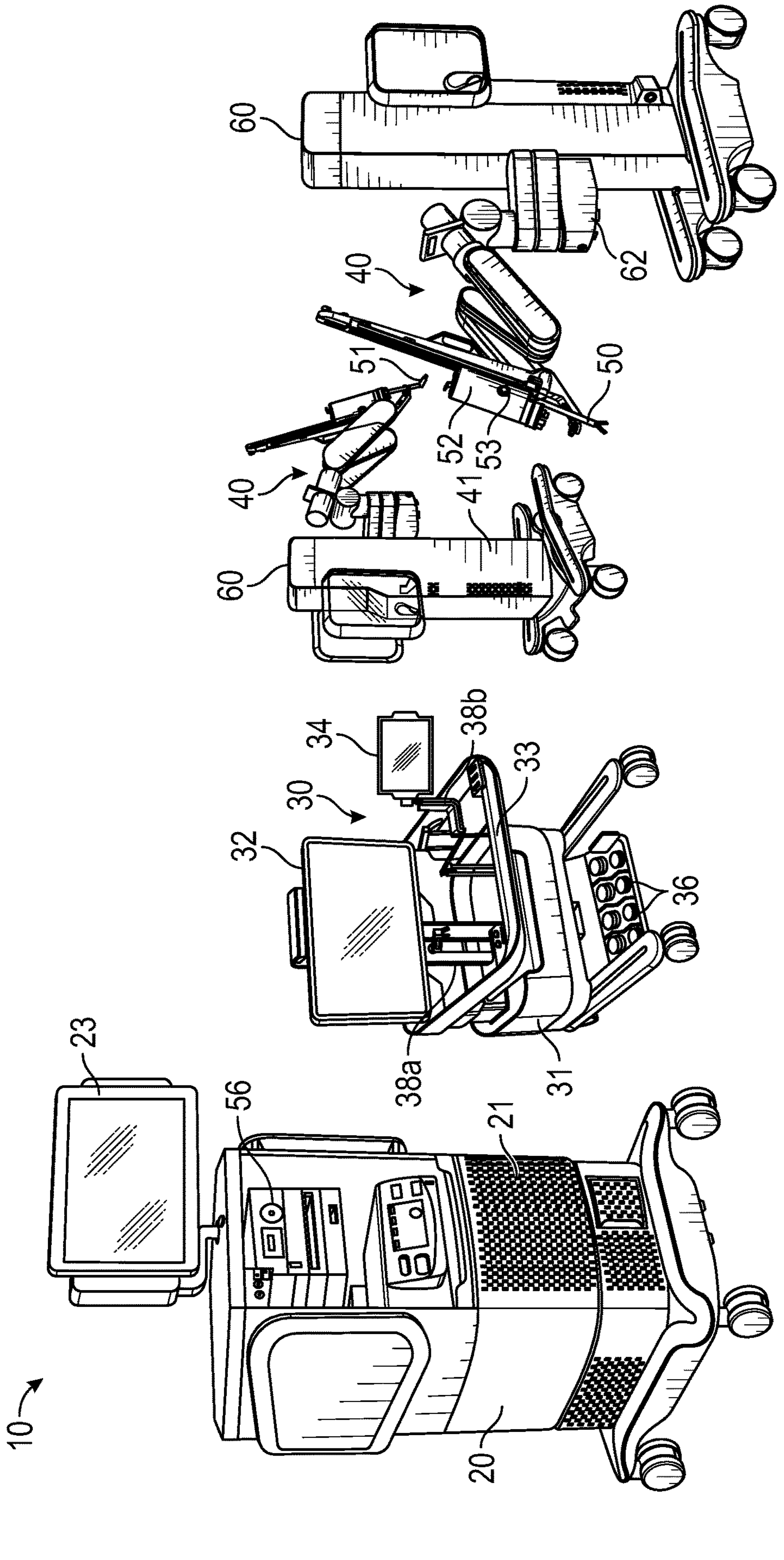
FIG. 1 is a schematic illustration of a surgical robotic system including a control tower, a console, and one or more surgical robotic arms according to an embodiment of the present disclosure.

With reference to FIG. 1, a surgical robotic system 10 includes a control tower 20, which is connected to all of the components of the surgical robotic system 10 including a surgical console 30 and one or more robotic arms 40. Each of the robotic arms 40 includes a surgical instrument 50 removably coupled thereto. Each of the robotic arms 40 is also coupled to a movable cart 60.

The surgical instrument 50 is configured for use during minimally invasive surgical procedures. In embodiments, the surgical instrument 50 may be configured for open surgical procedures. In embodiments, the surgical instrument 50 may be an endoscope configured to provide a video feed for the user. In further embodiments, the surgical instrument 50 may be an electrosurgical forceps configured to seal tissue by compression tissue between jaw members and applying electrosurgical current thereto. In yet further embodiments, the surgical instrument 50 may be a surgical stapler including a pair of jaws configured to grasp and clamp tissue whilst deploying a plurality of tissue fasteners, e.g., staples, and cutting stapled tissue.

Each of the robotic arms 40 may include a camera 51 configured to capture video of the surgical site. The camera 51 may be a stereoscopic camera and may be disposed along with the surgical instrument 50 on the robotic arm 40. The surgical console 30 includes a first display 32, which displays a video feed of the surgical site provided by camera 51 of the surgical instrument 50 disposed on the robotic arms 40, and a second display device 34, which displays a user interface for controlling the surgical robotic system 10. The surgical console 30 also includes a plurality of user interface devices, such as foot pedals 36 and a pair of handle controllers 38*a* and 38*b* which are used by a user to remotely control robotic arms 40.

The control tower 20 includes a display 23, which may be a touchscreen, and outputs on the graphical user interfaces (GUIs). The control tower 20 also acts as an interface between the surgical console 30 and one or more robotic arms 40. In particular, the control tower 20 is configured to control the robotic arms 40, such as to move the robotic arms 40 and the corresponding surgical instrument 50, based on a set of programmable instructions and/or input commands from the surgical console 30, in such a way that robotic arms 40 and the surgical instrument 50 execute a desired movement sequence in response to input from the foot pedals 36 and the handle controllers 38*a* and 38*b*.

Each of the control tower 20, the surgical console 30, and the robotic arm 40 includes a respective computer 21, 31, 41. The computers 21, 31, 41 are interconnected to each other using any suitable communication network based on wired or wireless communication protocols. The term "network," whether plural or singular, as used herein, denotes a data network, including, but not limited to, the Internet, Intranet, a wide area network, or a local area networks, and without limitation as to the full scope of the definition of communication networks as encompassed by the present disclosure. Suitable protocols include, but are not limited to, transmission control protocol/internet protocol (TCP/IP), datagram protocol/internet protocol (UDP/IP), and/or datagram congestion control protocol (DCCP). Wireless communication may be achieved via one or more wireless configurations, e.g., radio frequency, optical, Wi-Fi, Bluetooth (an open wireless protocol for exchanging data over short distances, using short length radio waves, from fixed and mobile devices, creating personal area networks (PANs), ZigBee® (a specification for a suite of high level communication protocols using small, low-power digital radios based on the IEEE 802.15.4-2003 standard for wireless personal area networks (WPANs)).

The computers 21, 31, 41 may include any suitable processor (not shown) operably connected to a memory (not shown), which may include one or more of volatile, non-volatile, magnetic, optical, or electrical media, such as read-only memory (ROM), random access memory (RAM), electrically-erasable programmable ROM (EEPROM), non-volatile RAM (NVRAM), or flash memory. The processor may be any suitable processor (e.g., control circuit) adapted to perform the operations, calculations, and/or set of instructions described in the present disclosure including, but not limited to, a hardware processor, a field programmable gate array (FPGA), a digital signal processor (DSP), a central processing unit (CPU), a microprocessor, and combinations thereof. Those skilled in the art will appreciate that the processor may be substituted for by using any logic processor (e.g., control circuit) adapted to execute algorithms, calculations, and/or set of instructions described herein.

Figure 2:
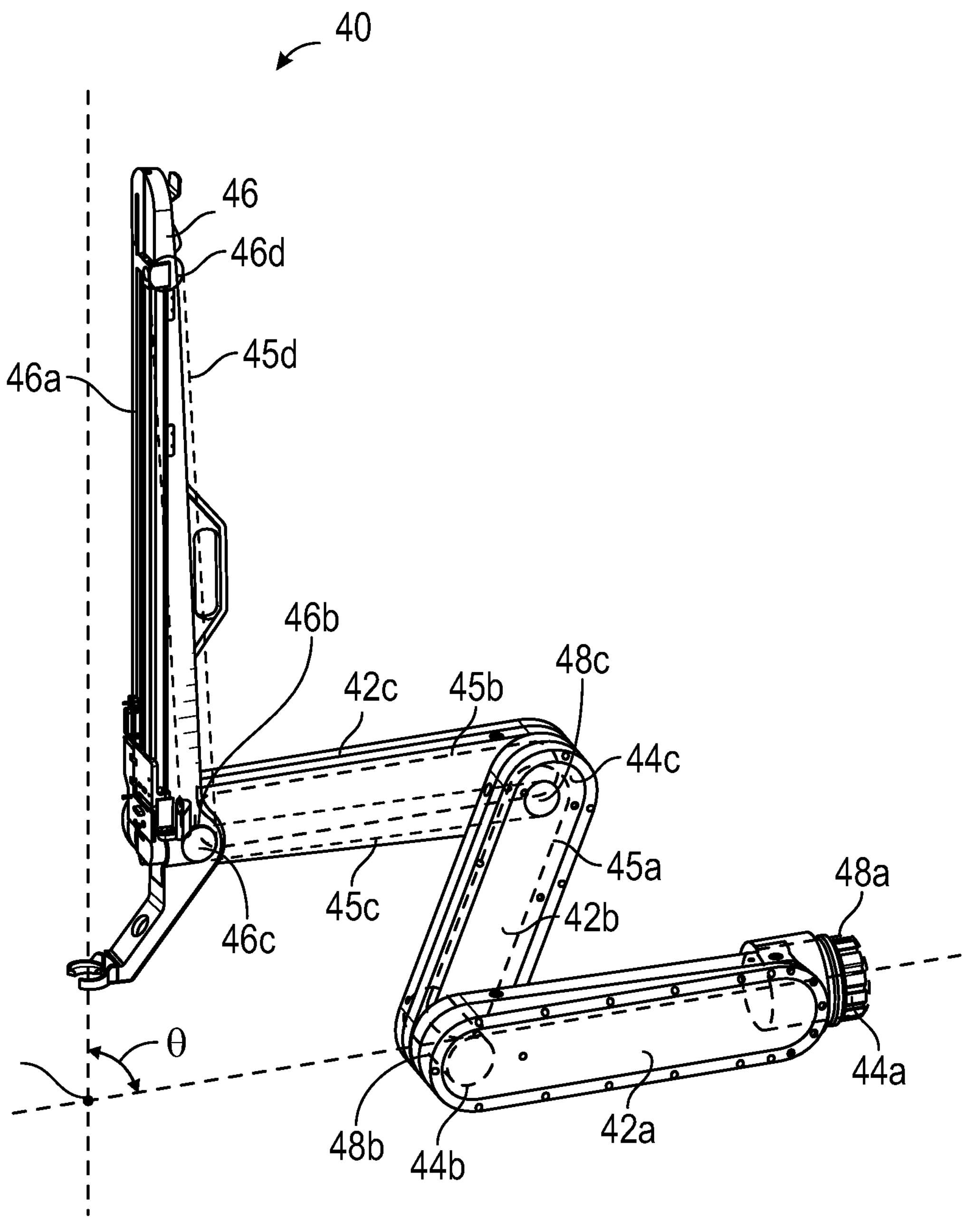
FIG. 2 is a perspective view of a surgical robotic arm of the surgical robotic system of FIG. 1 according to an embodiment of the present disclosure.
Figure 3:
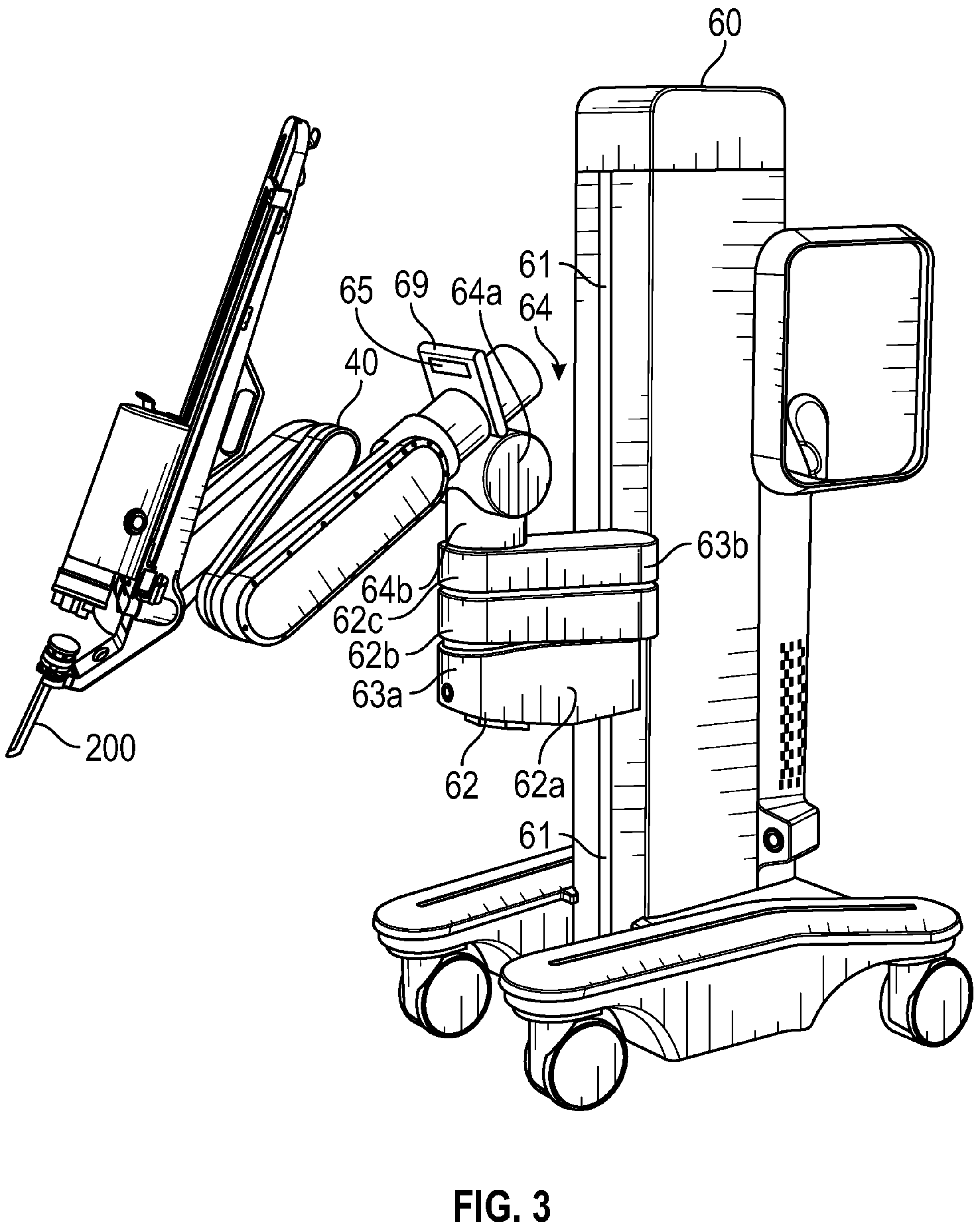
FIG. 3 is a perspective view of a setup arm with the surgical robotic arm of the surgical robotic system of FIG. 1 according to an embodiment of the present disclosure.

With reference to FIG. 2, each of the robotic arms 40 may include a plurality of links 42*a*, 42*b*, 42*c*, which are interconnected at joints 44*a*, 44*b*, 44*c*, respectively. The joint 44*a* is configured to secure the robotic arm 40 to the movable cart 60 and defines a first longitudinal axis. With reference to FIG. 3, the movable cart 60 includes a lift 61 and a setup arm 62, which provides a base for mounting of the robotic arm 40. The lift 61 allows for vertical movement of the setup arm 62. The movable cart 60 also includes a display 69 for displaying information pertaining to the robotic arm 40.

The setup arm 62 includes a first link 62*a*, a second link 62*b*, and a third link 62*c*, which provide for lateral maneuverability of the robotic arm 40. The links 62*a*, 62*b*, 62*c* are interconnected at joints 63*a* and 63*b*, each of which may include an actuator (not shown) for rotating the links 62*b* and 62*b* relative to each other and the link 62*c*. In particular, the links 62*a*, 62*b*, 62*c* are movable in their corresponding lateral planes that are parallel to each other, thereby allowing for extension of the robotic arm 40 relative to the patient (e.g., surgical table). In embodiments, the robotic arm 40 may be coupled to the surgical table (not shown). The setup arm 62 includes controls 65 for adjusting movement of the links 62*a*, 62*b*, 62*c* as well as the lift 61.

The third link 62*c* includes a rotatable base 64 having two degrees of freedom. In particular, the rotatable base 64 includes a first actuator 64*a* and a second actuator 64*b*. The first actuator 64*a* is rotatable about a first stationary arm axis which is perpendicular to a plane defined by the third link 62*c* and the second actuator 64*b* is rotatable about a second stationary arm axis which is transverse to the first stationary arm axis. The first and second actuators 64*a* and 64*b* allow for full three-dimensional orientation of the robotic arm 40.

Figure 5:
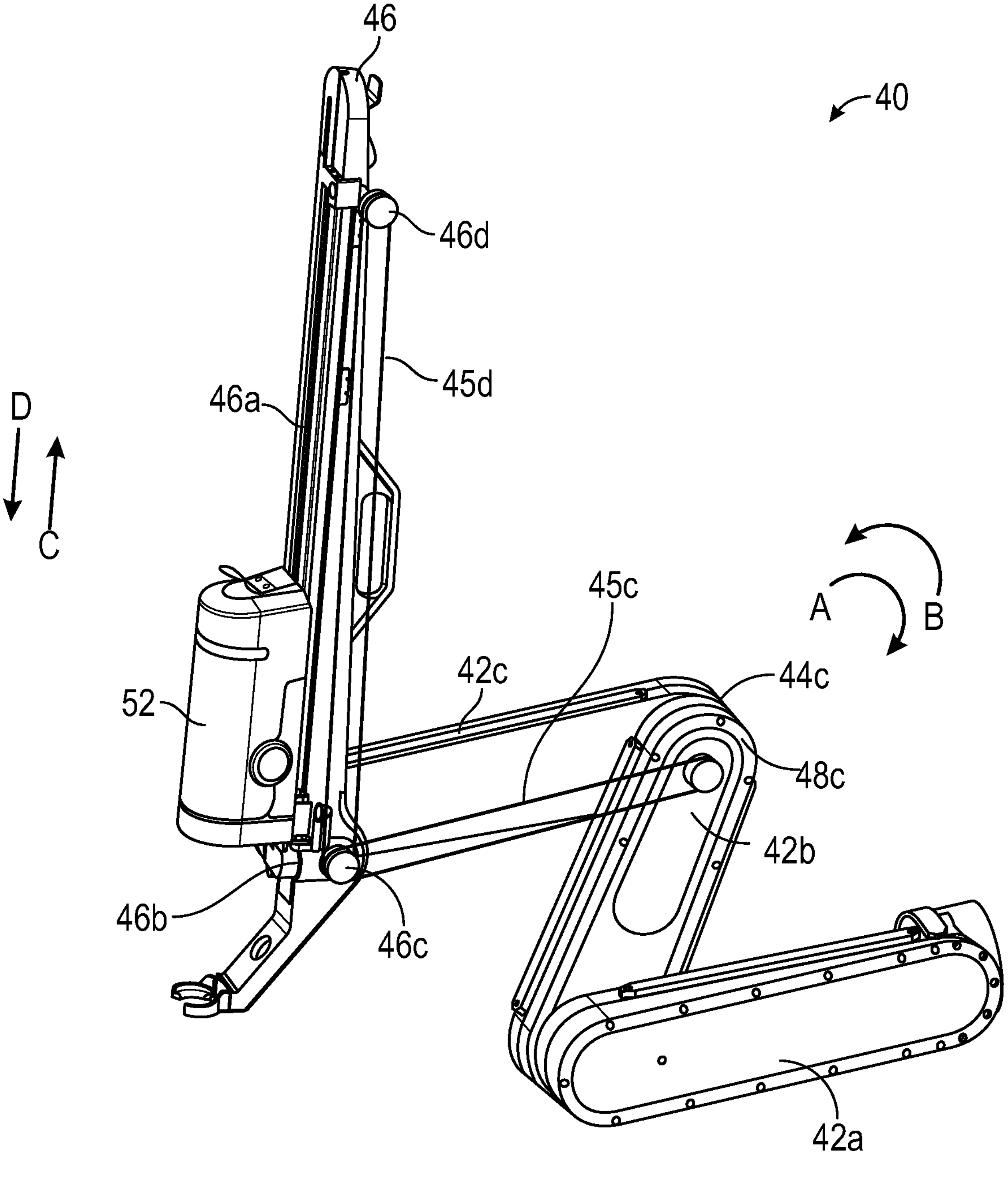
FIG. 5 is a perspective view of the surgical robotic arm of FIG. 2 schematically illustrating internal components thereof depicted externally for visibility.

With reference to FIG. 2, the robotic arm 40 also includes a holder 46 defining a second longitudinal axis and configured to receive the instrument drive unit 52 (FIG. 1) of the surgical instrument 50, which is configured to couple to an actuation mechanism of the surgical instrument 50. Instrument drive unit 52 transfers actuation forces from its actuators to the surgical instrument 50 to actuate components (e.g., end effectors) of the surgical instrument 50. The holder 46 includes a sliding mechanism 46*a*, which is configured to move the instrument drive unit 52 along the second longitudinal axis defined by the holder 46 in the direction of arrow "C" and the direction of arrow "D" (FIG. 5). The holder 46 also includes a joint 46*b*, which rotates the holder 46 relative to the link 42*c*.

The robotic arm 40 also includes a plurality of manual override buttons 53 disposed on the IDU 52 and the setup arm 62, which may be used in a manual mode. The clinician may press one or the buttons 53 to move the component associated with the button 53.

The joints 44*a* and 44*b* include an actuator 48*a* and 48*b* configured to drive the joints 44*a*, 44*b*, 44*c* relative to each other through a series of belts 45*a* and 45*b* or other mechanical linkages such as a drive rod, a cable, or a lever and the like. In particular, the actuator 48*a* is configured to rotate the robotic arm 40 about a longitudinal axis defined by the link 42*a*.

The actuator 48*b* of the joint 44*b* is coupled to the joint 44*c* via the belt 45*a*, and the joint 44*c* is in turn coupled to the joint 46*b* via the belt 45*b*. Joint 44*c* may include a transfer case coupling the belts 45*a* and 45*b*, such that the actuator 48*b* is configured to rotate each of the links 42*b*, 42*c* and the holder 46 relative to each other. More specifically, links 42*b*, 42*c*, and the holder 46 are passively coupled to the actuator 48*b* which enforces rotation about a pivot point "P" which lies at an intersection of the first axis defined by the link 42*a* and the second axis defined by the holder 46. Thus, the actuator 48*b* controls the angle θ between the first and second axes allowing for orientation of the surgical instrument 50. Due to the interlinking of the links 42*a*, 42*b*, 42*c*, and the holder 46 via the belts 45*a* and 45*b*, the angles between the links 42*a*, 42*b*, 42*c*, and the holder 46 are also adjusted in order to achieve the desired angle θ. In embodiments, some or all of the joints 44*a*, 44*b*, 44*c* may include an actuator to obviate the need for mechanical linkages.

With continued reference to FIG. 2 and with additional reference to FIG. 5, linear movement of the instrument drive unit 52 along the second longitudinal axis defined by the holder 46 in the direction of arrow "C" and the direction of arrow "D", and the components causing such movements, will now be described. As described above, the robotic arm 40 includes a first link 42*b* pivotably coupled to a second link 42*c* and a holder 46 pivotably coupled to the second link 42*c*. In an aspect, the robotic arm 40 includes one or more additional links, such as third link 42*a*. The first link 42*b* is coupled to the second link 42*c* at the first joint 44*c* and the holder 46 is coupled to the second link 42*c* at the second joint 46*b*. The third link 42*a* is coupled to the first link 42*b* at the third joint 44*b*.

The second link 42*c* includes a first belt 45*c*. The first link 42*b* integrates an actuator 48*c*, with its rotary output being coaxial to the first joint 44*c* and operably coupled to the first belt 45*c*. The holder 46 includes a first pulley 46*c*, a second pulley 46*d*, and a second belt 45*d* coupled to the first pulley 46*c* and the second pulley 46*d*. The first belt 45*c* is also operationally coupled to the first pulley 46*c*. The instrument drive unit 52 is operably coupled to the second belt 45*d* and is detachable therefrom. The instrument drive unit 52 is configured to move linearly along a longitudinal axis of the holder 46 (e.g., second longitudinal axis described above) and detachable couples a surgical instrument 50 to the robotic arm 40.

Rotation of the actuator 48*c* in a first direction "A" causes the instrument drive unit 52 to move along the longitudinal axis of the holder 46 in a first linear direction "C" and rotation of the actuator 48*c* in a second direction "B", opposite the first direction "A", causes the instrument drive unit 52 to move along the longitudinal axis of the holder 46 in a second linear direction "D" opposite the first linear direction "C".

The actuator 48*c* may be mounted into the first link 42*b* and its output is positioned at the first joint 44*c* and the first pulley 46*c* is positioned at the second joint 46*b*. The first pulley 46*c* is coupled to the actuator 48*c* via the first belt 45*c* of the second link 42*c*. A second actuator 48*b* is positioned at the third joint 44*b* and is coupled to a third belt 45*a*, which is included in the first link 42*b*, and to a fourth belt 45*b*, which is included in the second link 42*c*, such that actuation of the second actuator 48*b* causes the first link 42*b* to pivot relative to the third link 42*a* and the second link 42*c*. In other words, this movement mechanism consist of the second actuator 48*b* (mounted to the third link 42*a*) and two drive mechanisms (e.g., cables, belts) of which the first (e.g., third belt 45*a*) connects the third link 42*a* with the second link 42*c* and the second (e.g., fourth belt 45*b*) connects the first link 42*b* with the holder 46.

As the first link 42*b* pivots relative to the third link 42*a*, the angle between the holder 46 and the third link 42*a* and the angle between the holder 46 and the second link 42*c* remains unchanged. Additionally, according to the disclosed configuration of the robotic arm 40, as any of the first link 42*b*, second link 42*c*, third link 42*a*, and the holder 46 are pivoted relative to each other, the position of the instrument drive unit 52 along the longitudinal axis of the holder 46 remains unchanged without the need to control the actuator 48*c* to compensate for movements of any of the first link 42*b*, second link 42*c*, third link 42*a*, and the holder 46.

The positioning of the actuator 48*c* in the first link 42*b* (e.g., proximate the first joint 44*c*) reduces the mass, inertia, and size of the tip of the robotic arm 40 (e.g., a region proximate the instrument drive unit 52 when the robotic arm 40 is in an extended condition), thereby enabling easier manipulation of the robotic arm 40. In particular, a lighter distal-most joint, enabled by virtue of the more proximal positioning of the actuator 48*c*, allows for less strain on the joints of the robotic arm 40 resulting in easier manipulation of the links due to a lesser degree of gravity compensation required during movement of the robotic arm 40 and its components.

Figure 4:
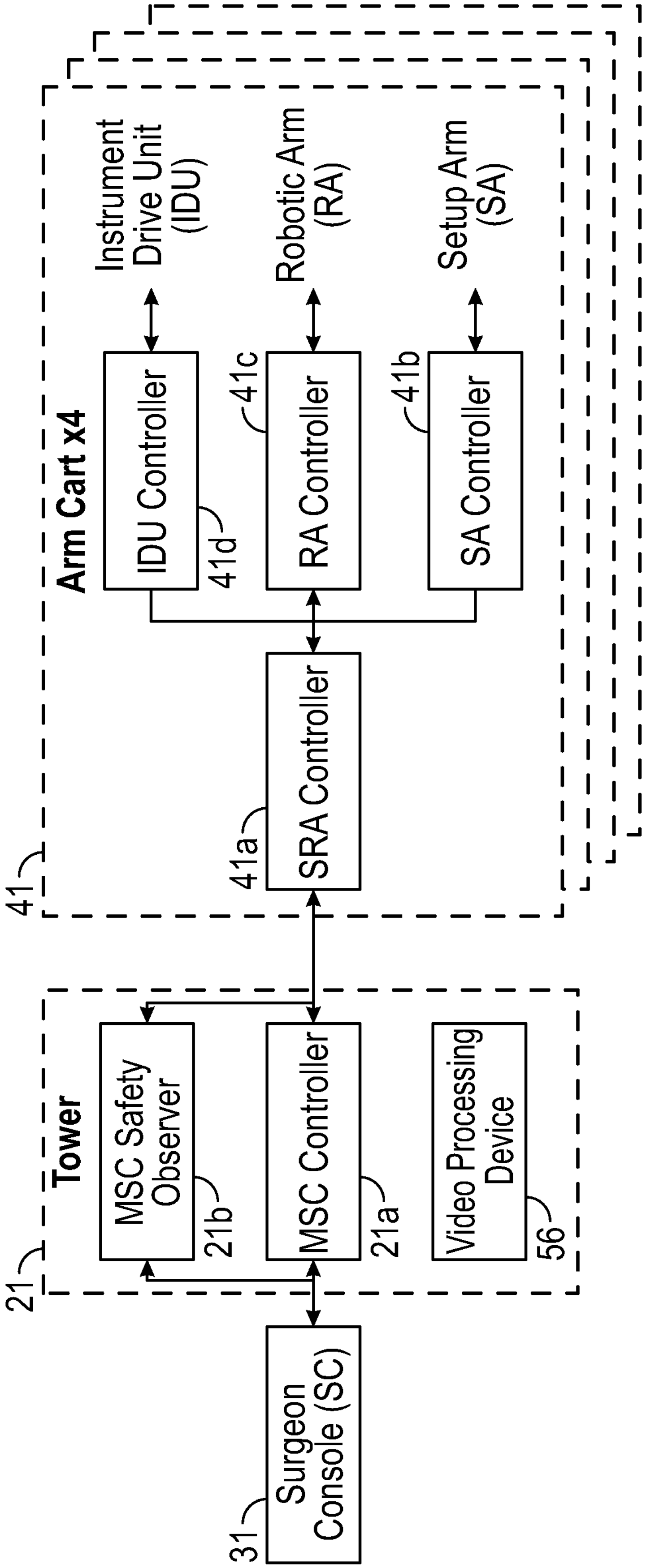
FIG. 4 is a schematic diagram of a computer architecture of the surgical robotic system of FIG. 1 according to an embodiment of the present disclosure.

With reference to FIG. 4, each of the computers 21, 31, 41 of the surgical robotic system 10 may include a plurality of controllers, which may be embodied in hardware and/or software. The computer 21 of the control tower 20 includes a controller 21_a_ and safety observer 21_b_. The controller 21_a_ receives data from the computer 31 of the surgical console 30 about the current position and/or orientation of the handle controllers 38_a_ and 38_b_ and the state of the foot pedals 36 and other buttons. The controller 21_a_ processes these input positions to determine desired drive commands for each joint of the robotic arm 40 and/or the instrument drive unit 52 and communicates these to the computer 41 of the robotic arm 40. The controller 21_a_ also receives back the actual joint angles and uses this information to determine force feedback commands that are transmitted back to the computer 31 of the surgical console 30 to provide haptic feedback through the handle controllers 38_a_ and 38_b_. The safety observer 21_b_ performs validity checks on the data going into and out of the controller 21_a_ and notifies a system fault handler if errors in the data transmission are detected to place the computer 21 and/or the surgical robotic system 10 into a safe state.

The computer 41 includes a plurality of controllers, namely, a main cart controller 41_a_, a setup arm controller 41_b_, a robotic arm controller 41_c_, and an instrument drive unit (IDU) controller 41_d_. The main cart controller 41_a_ receives and processes joint commands from the controller 21_a_ of the computer 21 and communicates them to the setup arm controller 41_b_, the robotic arm controller 41_c_, and the IDU controller 41_d_. The main cart controller 41_a_ also manages instrument exchanges and the overall state of the movable cart 60, the robotic arm 40, and the instrument drive unit 52. The main cart controller 41_a_ also communicates actual joint angles back to the controller 21_a_.

The setup arm controller 41_b_ controls each of joints 63_a_ and 63_b_, and the rotatable base 64 of the setup arm 62 and calculates desired motor movement commands (e.g., motor torque) for the pitch axis and controls the brakes. The robotic arm controller 41_c_ controls each joint 44_a_ and 44_b_ of the robotic arm 40 and calculates desired motor torques required for gravity compensation, friction compensation, and closed loop position control of the robotic arm 40. The robotic arm controller 41_c_ calculates a movement command based on the calculated torque. The calculated motor commands are then communicated to one or more of the actuators 48_a_ and 48_b_ in the robotic arm 40. The actual joint positions are then transmitted by the actuators 48_a_ and 48_b_ back to the robotic arm controller 41_c_.

The IDU controller 41_d_ receives desired joint angles for the surgical instrument 50, such as wrist and jaw angles, and computes desired currents for the motors in the instrument drive unit 52. The IDU controller 41_d_ calculates actual angles based on the motor positions and transmits the actual angles back to the main cart controller 41_a_.

The robotic arm 40 is controlled as follows. Initially, a pose of the handle controller controlling the robotic arm 40, e.g., the handle controller 38_a_, is transformed into a desired pose of the robotic arm 40 through a hand eye transform function executed by the controller 21_a_. The hand eye function, as well as other functions described herein, is/are embodied in software executable by the controller 21_a_ or any other suitable controller described herein. The pose of one of the handle controller 38_a_ may be embodied as a coordinate position and role-pitch-yaw ("RPY") orientation relative to a coordinate reference frame, which is fixed to the surgical console 30. The desired pose of the surgical instrument 50 is relative to a fixed frame on the robotic arm 40. The pose of the handle controller 38_a_ is then scaled by a scaling function executed by the controller 21_a_. In embodiments, the coordinate position is scaled down and the orientation is scaled up by the scaling function. In addition, the controller 21_a_ also executes a clutching function, which disengages the handle controller 38_a_ from the robotic arm 40. In particular, the controller 21_a_ stops transmitting movement commands from the handle controller 38_a_ to the robotic arm 40 if certain movement limits or other thresholds are exceeded and in essence acts like a virtual clutch mechanism, e.g., limits mechanical input from effecting mechanical output.

The desired pose of the robotic arm 40 is based on the pose of the handle controller 38_a_ and is then passed by an inverse kinematics function executed by the controller 21_a_. The inverse kinematics function calculates angles for the joints 44_a_, 44_b_, 44_c_ of the robotic arm 40 that achieve the scaled and adjusted pose input by the handle controller 38_a_. The calculated angles are then passed to the robotic arm controller 41_c_, which includes a joint axis controller having a proportional-derivative (PD) controller, the friction estimator module, the gravity compensator module, and a two-sided saturation block, which is configured to limit the commanded torque of the motors of the joints 44_a_, 44_b_, 44_c_.

It will be understood that various modifications may be made to the embodiments disclosed herein. In embodiments, the sensors may be disposed on any suitable portion of the robotic arm. Therefore, the above description should not be construed as limiting, but merely as exemplifications of various embodiments. Those skilled in the art will envision other modifications within the scope and spirit of the claims appended thereto.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A surgical robotic system comprising:

a movable cart; and a robotic arm operably coupled to the movable cart, the robotic arm including:

a first link pivotally coupled to a second link at a first joint and including an actuator, the second link including a first belt operably coupled to the actuator, wherein the actuator is integrated into the first link and configured to produce an output oriented coaxially with the first joint;

a holder pivotally coupled to the second link at a second joint, the holder including a first pulley coupled to the first belt at the second joint, a second pulley, and a second belt coupled to the first pulley and the second pulley; and an instrument drive unit operably coupled to the second belt and configured to move linearly along a longitudinal axis of the holder in response to the output of the actuator transmitted through the first belt, through the first joint, and through the second joint to the second belt.

2. The surgical robotic system according to claim 1, wherein rotation of the actuator in a first direction causes the instrument drive unit to move along the longitudinal axis of the holder in a first linear direction and wherein rotation of the actuator in a second direction causes the instrument drive unit to move along the longitudinal axis of the holder in a second linear direction opposite the first linear direction.

3. The surgical robotic system according to claim 1, wherein the instrument drive unit is removably coupled to the second belt.

4. The surgical robotic system according to claim 1, further comprising a surgical instrument operably coupled to the instrument drive unit.

5. The surgical robotic system according to claim 1, further comprising a third link pivotally coupled to the first link at a third joint.

6. The surgical robotic system according to claim 5, further comprising a second actuator at the third joint, wherein the first link further includes a third belt operably coupled to the second actuator, and wherein actuation of the second actuator causes the first link to pivot relative to the third link and the second link.

7. The surgical robotic system according to claim 1, wherein an angle between the holder and the first link does not change upon movement of the second link relative to the first link.

8. A robotic arm for a surgical robotic system, the robotic arm comprising:

a first link pivotally coupled to a second link at a first joint and including an actuator, the second link including a first belt operably coupled to the actuator, wherein the actuator is integrated into the first link and configured to produce an output oriented coaxially with the first joint;

a holder pivotally coupled to the second link at a second joint, the holder including a first pulley coupled to the first belt at the second joint, a second pulley, and a second belt coupled to the first pulley and the second pulley; and an instrument drive unit operably coupled to the second belt and configured to move linearly along a longitudinal axis of the holder in response to the output of the actuator transmitted through the first belt, through the first joint, and through the second joint to the second belt.

9. The robotic arm according to claim 8, wherein rotation of the actuator in a first direction causes the instrument drive unit to move along the longitudinal axis of the holder in a first linear direction and wherein rotation of the actuator in a second direction causes the instrument drive unit to move along the longitudinal axis of the holder in a second linear direction opposite the first linear direction.

10. The robotic arm according to claim 8, wherein the instrument drive unit is removably coupled to the second belt.

11. The robotic arm according to claim 8, further comprising a surgical instrument operably coupled to the instrument drive unit.

12. The robotic arm according to claim 8, further comprising a third link pivotally coupled to the first link at a third joint.

13. The robotic arm according to claim 12, further comprising a second actuator disposed at the third joint.

14. The robotic arm according to claim 13, wherein the first link further includes a third belt operably coupled to the second actuator.

15. The robotic arm according to claim 13, wherein actuation of the second actuator causes the first link to pivot relative to the third link and the second link.

16. The robotic arm according to claim 8, wherein an angle between the holder and the first link does not change upon movement of the second link relative to the first link.

* * * * *